United States Patent [19]
Gumaste et al.

[11] Patent Number: 5,840,062
[45] Date of Patent: Nov. 24, 1998

[54] SOLID STATE FLUID DELIVERY SYSTEM

[76] Inventors: Anand V. Gumaste, 7 Ardsley Ct., Robbinsville, N.J. 08691; Andrew L. Abrams, 26 Imperial Ave., Westport, Conn. 06880; Scott Fleming, 18 Riverview Dr., Ewing, N.J. 08628

[21] Appl. No.: 555,207
[22] Filed: Nov. 8, 1995
[51] Int. Cl.⁶ ..................................................... A61M 5/30
[52] U.S. Cl. ............................................................ 604/68
[58] Field of Search ................................ 604/20, 30–34, 604/50, 52, 53, 65–67, 246–249; 128/DIG. 12, 13

[56] References Cited

U.S. PATENT DOCUMENTS

| | | |
|---|---|---|
| 4,787,888 | 11/1988 | Fox . |
| 4,944,659 | 7/1990 | Labbe et al. ............................. 417/322 |
| 5,007,438 | 4/1991 | Tachibana et al. . |
| 5,094,594 | 3/1992 | Brennan .................................... 604/20 |
| 5,415,629 | 5/1995 | Henley . |
| 5,474,527 | 12/1995 | Bettinger .................................... 604/19 |

*Primary Examiner*—Michael Buiz
*Assistant Examiner*—Manuel Mendez
*Attorney, Agent, or Firm*—Hayes, Soloway, Hennessey, Grossman & Hage, P.C.

[57] ABSTRACT

An apparatus and method are disclosed that utilize piezoelectric materials as part of a delivery system capable of the rapidly repetitive dispensing of a fluid to an intended target site. In a particular embodiment, the appartus contemplates a solid state needleless injection system which comprises a first housing structure having a dispensing chamber of variable volume capacity and at least one nozzle element for fluid discharge, and a fluid reservoir operatively connected to the first housing structure, and a second housing structure containing at least one piezoelectric actuator. A valve means is disposed between the fluid reservoir and the dispensing chamber to control the flow of said fluid therebetween. The fluid which may be a medication, is forced out of the dispensing chamber through an injection port upon actuation of the piezoelectric actuator. The piezoelectric actuator interacts with the dispensing chamber in such a manner that the overall capacity of the dispensing chamber may be altered by altering the degree of actuation of the piezoelectric actuator.

22 Claims, 3 Drawing Sheets

SOLID STATE FLUID DELIVERY SYSTEM

FIELD OF THE INVENTION

The present invention relates generally to fluid delivery systems and, more particularly, to solid state delivery systems that do not require a needle-like nozzle and that utilize piezoelectric materials to achieve the rapid injection of accurate small quantities of fluid.

BACKGROUND OF THE INVENTION

The delivery of fluids, including within the definition of this term liquids, solid particles and gases, in a variety of contexts has progressed in recent years to embrace various automated transport and delivery systems. Specifically, the development of equipment requiring rapid delivery of microquantities of fluid to a particular location or target, finds it application to such diverse areas as, for example, fuel delivery for internal combustion and turbine-type engines, the delivery of reagents in chemical and biological research and diagnostic procedures, and the delivery of microquantities of medicaments to patents for therapeutic purposes. In all of these instances, the extant technology and equipment is limited in its ability to define and control parameters for the precise delivery of exceedingly small volumes of liquid in rapid repeatable fashion. The problems and corresponding needs for improved equipment are particularly acute in the area of medicament delivery, as described in greater detail below.

Medications are injected through the skin to provide therapeutic effects which are more efficient or unobtainable through other drug delivery routes. Some reasons for injecting medications are: 1.) chemical destruction of the medication by the gastrointestinal tract; 2.) poor absorption; 3.) patient too sick or too young to take the medicine orally; and 4.) need for rapid action of the drug.

The most commonly used device to inject a medication is a hypodermic needle attached to a plunger syringe. These syringes come in a variety of sizes and can be automated by connecting them to a pump mechanism, or a pump designed for injection can be utilized. Such pumps are used primarily for intravascular or intrathecal delivery.

A number of needleless injection systems presently exist. These systems use a compressed gas, either $CO_2$ or compressed air. The gas is released at high pressure on demand and acts on a movable piston which forces medication out of the nozzle of the syringe. The resulting high velocity jet stream deposits the medication under the skin of a patient. All needleless injection systems have the advantage of not requiring "sharps" which are considered a bio-hazard and require careful disposal.

Present needleless injection systems are generally large and noisy. They require either the cocking of a spring mechanism or an attachment to a $CO_2$ source. Use of these devices requires a trained, skilled operator. Also, they must be disassembled to be cleaned. Furthermore, they cannot be programmed for automated delivery.

Certain devices that assist in the administration of medication and which utilize piezoelectric materials for performing certain administration functions have been described. For example, U.S. Pat. No. 4,787,888 to Fox, U.S. Pat. No. 5,094,594 to Brennan, U.S. Pat. No. 5,415,629 to Henley, and U.S. Pat. No. 5,007,438 to Tachibana et al. are all directed toward the administration of medications and/or the use of piezoelectric materials for such administration or otherwise.

More particularly, U.S. Pat. No. 4,787,888 to Fox discloses a bandage assembly for percutaneous administration of medication wherein a piezoelectric material is utilized so as to generate sonic vibrations for assisting the medication to be absorbed into the skin of a patient. It should be noted that this patent fails to disclose the use of piezoelectric materials as injection means wherein medication is forcibly introduced through the skin.

U.S. Pat. No. 5,094,594 to Brennan discloses a piezoelectric pumping device wherein piezoelectric material is utilized as a pumping means in conjunction with an electrophoretic unit. The Brennan apparatus is complex and cumbersome, and lacks the applicability to a needleless medicament injection system, and particularly such a system as is capable of forcibly introducing medication through the skin of a patient.

U.S. Pat. No. 5,415,629 to Henley discloses a programmable apparatus for the transdermal delivery of medication wherein piezoelectric elements are utilized for providing ultrasonic vibrations which enhance penetration of the medication into the skin of a patient. It should be noted that this patent fails to disclose the use of piezoelectric materials as injection means wherein medication is forcibly introduced through the skin.

U.S. Pat. No. 5,007,438 to Tachibana et al. disclose an endermic application kit for external medicines wherein an ultrasonic oscillation is utilized to enhance the absorption of medication by the skin of a patient. It should be noted that this patent fails to disclose the use of piezoelectric materials as injection means wherein medication is forcibly introduced through the skin of a patient. In fact, this patent fails to disclose the use of piezoelectric materials in any manner.

Although the above-mentioned patents are generally directed toward the metered delivery of fluids, including in some instances, medications, and illustrate prior applications of piezoelectric materials for their specific objectives, none are directed toward providing a method for utilizing piezoelectric materials as injection means wherein medication is forcibly introduced through the skin of a patient. Such a method would realize all of the benefits of a needleless injection system along with many other advantages as detailed below.

More generally, the development of a simple and inexpensive delivery system that can transfer small amounts of fluid on a rapid, quiet, accurate and repeatable basis would be highly valued not only in regard to the injection of medicaments, but in the other commercial and industrial areas listed above where similar needs exist. Accordingly, it is toward the fulfillment of the needs expressed above that the present invention is directed.

SUMMARY OF THE INVENTION

In its broadest aspect the present invention extends to an apparatus and corresponding method for the rapid delivery of a fluid. The apparatus of the invention comprises at least one first housing having walls defining a dispensing chamber, that may be of adjustable size for containing the fluid to be dispensed, at least one nozzle element defined in at least one of said walls for the discharge therethrough of said fluid, and a second housing which, in one embodiment, may be adapted for detachable association to said first housing, including pump means for forcing a predetermined volume of said fluid out of said dispensing chamber and through said nozzle element. The pump means comprises at least one piezoelectric element adapted to cooperate with said first housing to impose a predetermined pressure within said dispensing chamber to force the predetermined volume of said fluid through the nozzle element and to deliver said fluid to the intended target.

An actuator for the excitation of the piezoelectric elements is included, which may include means for controlling the amount and temporal schedule for dispensing of said fluid. For example, the actuator of the invention may include a battery unit for portable application of the apparatus, and circuitry including a programmable controller for pre-setting the amount, frequency and duration of fluid dispensing. This capability has particular value in the instance where the inventive apparatus is applied to the administration of medication, whether in a clinical setting or in a constant and personal setting.

The invention also extends to a method for utilizing piezoelectric materials as a pump means as described above, wherein the excitation of the piezoelectric element forces the fluid to egress the dispensing chamber and delivers the fluid to its intended target. More particularly, the method comprises the sequential excitation of plural piezoelectric elements, each associated with respective fluid chambers that are in communication with each other, to convey a predetermined amount of fluid from a reservoir to the chamber from which the fluid is finally dispensed to its intended delivery site. The application of this sequential arrangement facilitates both speed and accuracy, as precise metering and rapidly repeatable delivery are enabled.

In a preferred embodiment, the invention comprises an apparatus for the rapid and accurate delivery of medical reagents and medicaments, and particularly extends to a needleless injection system which is capable of forceably delivering medication transdermally to a patient. A particular apparatus comprises a solid state needleless injection system which comprises a first housing having walls defining a dispensing chamber, a valve assembly comprising a cooperating valve stop and valve seat formed in said first housing and located in fluid communication with said dispensing chamber, and a fluid reservoir operatively connected to the first housing; and a second housing defining walls one of which is in communication with said first housing, which second housing contains at least one piezoelectric element adapted to communicate with the first housing to dispense the fluid from the system. In a particular embodiment, the first and second housings define common walls that may be detachably attached to each other, and an additional piezoelectric element is contained within the second housing and is positioned for operative communication with the valve assembly located in the second housing, to alternately permit and prevent fluid from entering said dispensing chamber from said fluid reservoir.

The fluid reservoir provides fluid medication to the dispensing chamber through the valve assembly and the fluid medication is forced out of the dispensing chamber through one or more injection ports upon actuation of the piezoelectric actuator associated with the dispensing chamber. The piezoelectric actuator interacts with the dispensing chamber by impacting the wall of the first housing that is contiguous thereto, in such a manner that the overall capacity of the dispensing chamber may be altered by altering the degree of actuation of the piezoelectric actuator. Thus, the piezoelectric actuator acts as a driver which forces the fluid medication out of the dispensing chamber whereby it is forcibly introduced through the skin of a patient.

The valve assembly comprises a valve stop that is preferably formed in the portion of the wall of the first housing that is proximate the valve seat, and as stated above, a second piezoelectric element is preferably contained within the first housing for controlling the position of the valve stop within the valve seat and hence the fluid flow between the fluid reservoir and the dispensing chamber.

The apparatus of the present invention may be constructed as a portable unit using battery operation, in the instance where it is used for the delivery of medication to an ambulatory individual. Further, the first housing including the fluid reservoir and the dispensing chamber may be fabricated as a unit that is adapted to be detached from the second housing. In a further embodiment, the second housing may be discarded after all of the fluid is expelled. The apparatus may also include programming capability, so that an extended schedule of delivery can be preset, and sufficient medication supplied, to reduce periodic inspection of the device and replenishment of the medicament.

The use of piezoelectric actuation to mechanically force the discrete volume of fluid rapidly and at high pressure, together with the simplified construction of the apparatus makes the manufacture and use of the present apparatus particularly attractive, and further augments the advantages thereof. Medications dispensed with the present apparatus may be delivered in small doses within short time intervals, and may thereby provide a more precise administration of a medication.

Accordingly, a principal object of the present invention is to provide a method and apparatus for the rapid and efficient delivery of fluids to target destinations, that are simple and economical to manufacture and use.

It is a further object of the present invention to provide an apparatus as aforesaid, that utilizes piezoelectric materials as a pump or injection means capable of forcibly delivering the fluid to the target destination.

It is a still further object of the present invention to provide an injection system that utilizes the properties of piezoelectric materials to respond rapidly to applied potentials, and to apply them as valves and powerful pumps and to assemble them as a unit.

Another object of the present invention is to provide a needleless, quiet, compact, inexpensive, easy to use, battery operated injection system, that is useful for the delivery of medication to a patient.

Another object of the present invention is to reduce medication delivery pain by many small low volume injections.

Another object of the present invention is to reduce the skill required by an operator of an injection system, and allow self medication injection, or medication injection by persons not specially trained.

Another object of the present invention is to provide an injection system which would allow medications which are given orally, rectally, or by other means for convenient home delivery to be delivered comfortably, and to provide all the benefits of transcutaneous drug delivery.

Another object of the present invention is to have programmability, and the possibility of continuous, or predetermined interval, medication delivery by an attached system.

Other objects and advantages of the present invention will become apparent to those skilled in the art from a review of the following detailed description and claims, in conjunction with the accompanying drawings which are appended hereto.

BRIEF DESCRIPTION OF THE DRAWINGS

In order to facilitate a fuller understanding of the present invention, reference is now be made to the appended drawings. The drawings should not be construed as limiting the present invention, but are intended to be exemplary only.

DETAILED DESCRIPTION OF THE PRESENT INVENTION

In its broadest aspect, the present invention relates to a delivery system for fluids, including powders, liquids and gases, that is capable of rapidly repetitive discharge of a precise and minute amount of such fluid on a continuous basis. Such a system finds particular application in a variety of contemporary industrial settings, extending from machinery design and operation, to medical devices for the administration of reagents and medications.

Accordingly, the apparatus of the invention comprises: at least one first housing having walls defining a dispensing chamber of adjustable volume for said fluid, and at least one nozzle element defined in one of said walls for the discharge of said fluid; at least one second housing adapted in one embodiment for detachable association with said first housing, including pump means comprising at least one piezoelectric element for forcing a predetermined quantity of said fluid out of said dispensing chamber and through said at least one nozzle element; and actuation means including controller means for exciting said pump means to force said fluid out of said dispensing chamber, and for controlling the operation of said pump means.

A particular embodiment of the contemplated apparatus is illustrated herein in relation to an apparatus for the needleless delivery of medication, and the following description is presented in detailed exposition of that application and embodiment. It is to be understood, however, that the features and principles of the invention extend beyond the following nonlimiting illustration.

Figure 1:
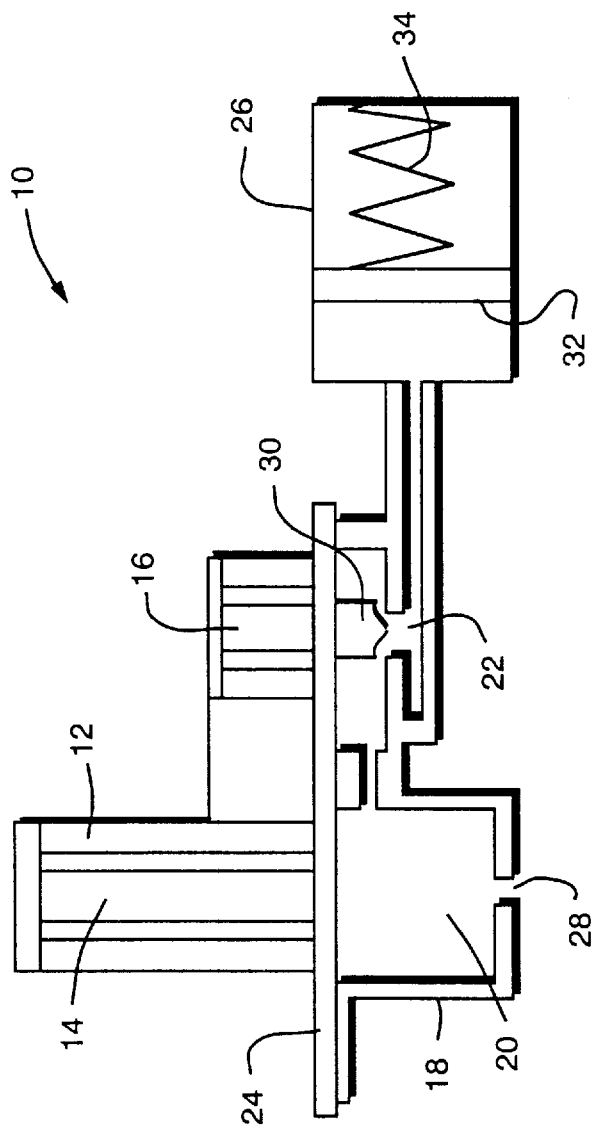
FIG. 1 is a functional block diagram of a solid state fluid delivery system according to a particular embodiment of the present invention.

Referring to the figures wherein like numerals designate like parts, and particularly to FIG. 1, there is shown a solid state needleless injection system 10 according to the present invention that utilizes piezoelectric materials so as to provide a force that is capable of injecting matter contained within a dispensing chamber through the skin of a patient. The solid state needleless injection system 10 comprises a second housing structure 12 containing a first piezoelectric element 14 and a second piezoelectric element 16, both elements 14 and 16 functioning as actuators of pumping movement; and a first housing structure 18 defining a dispensing chamber 20 of adjustable volume. Such volume adjustment may be accomplished by means of a deformable wall 24 which may be a flexible membrane, or by the disposition within chamber 20 of a wall having inward spring bias, such as that illustrated with reference to fluid reservoir 26, described below. Accordingly, the invention should not be limited to the specific adjustment capability and means illustrated herein.

Housing 18 includes a valve assembly comprising a valve seat 22, and a fluid reservoir 26 operatively connected to housing 18. The dispensing chamber 20, and hence the second housing structure 18, has at least one injection port 28 formed therein near the bottom thereof. The valve assembly also includes a valve stop 30 associated with deformable wall 24 as illustrated and located proximate to valve seat 22 and the second piezoelectric element 16. The fluid reservoir 26 has a plunger 32, and a biasing member, such as a piezoelectric element, or a spring 34 as illustrated, may be disposed therein to force fluids such as fluid medications that are contained therein into housing structure 18.

In a particular embodiment, the solid state needleless injection system 10 comprises two main parts: 1.) the second housing structure 12 containing the first piezoelectric actuator 14 and the second piezoelectric actuator 16, which is reusable; and 2.) a disposable cassette-like unit comprising the first housing structure 18 as described above, including fluid reservoir 26.

In operation, the second piezoelectric element 16, and hence the valve stop 30, is first retracted so as to allow fluid in the fluid reservoir 26 to flow through the valve seat and into the dispensing chamber 20. The first piezoelectric element 14 is then retracted so that the dispensing chamber 20 is totally filled. Next, the second piezoelectric element 16 is excited so that the valve stop 30 seals the valve seat 22 thereby stopping the fluid from flowing in either direction between the fluid reservoir 26 and the dispensing chamber 20. The first piezoelectric element 14 is then excited so that the volume of the dispensing chamber 20 is rapidly decreased and the fluid contained therein is displaced at high pressure. Thus, the fluid is forced out of the dispensing chamber 20 through the injection port 28 at a pressure sufficient in the instance of a medication, to penetrate the skin of a patient. This cycle can be repeated at various rates, but it is preferably repeated within the 100 to 2000 Hz range.

As previously mentioned, more than one injection port 28 can be provided in the dispensing chamber 20, and hence in the first housing structure 18. Such would allow for a more widespread injection area which would reduce discomfort and irritation at an injection site. It should be noted that each injection port 28 is typically 0.001 inches in diameter.

Both the second housing structure 12 and the first housing structure 18 may be fabricated of a variety of rigid materials, such as plastic or metal. In the instance where the fluid chamber 20 is compressible, a deformable wall 24 is included that may be fabricated of a variety of flexible materials, such as clear silicon. It should further be noted that the valve stop 30 may be separate from the wall 24.

Both the first piezoelectric element 14 and the second piezoelectric element 16 may be fabricated from a variety of piezoelectric materials, such as lead-zirconate/lead titanate (PZT). It should be noted, however, that the second piezoelectric actuator 16 may be replaced with a typical electromechanical actuator (not shown) comprising a magnet and a coil.

Figure 2:
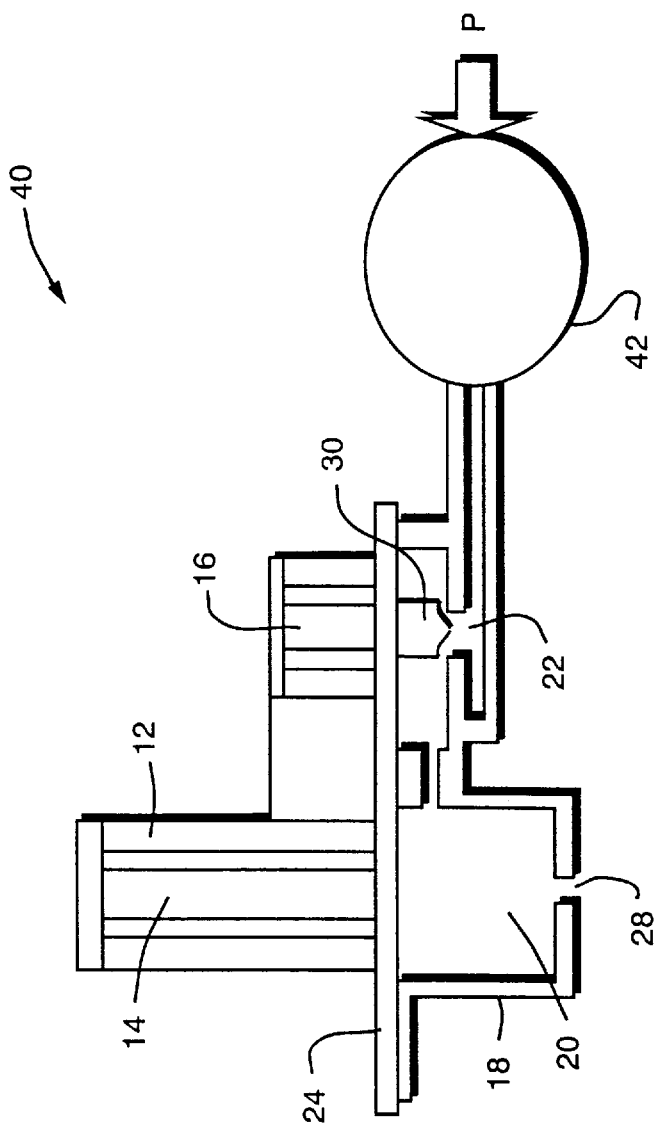
FIG. 2 is a functional block diagram of the delivery system shown in FIG. 1 with an alternate fluid reservoir.

The fluid reservoir 26 may be fabricated of a variety of materials, such as plastic. Also, the fluid reservoir 26 may take many different forms. For instance, referring to FIG. 2, there is shown a second embodiment of a solid state needleless injection system 40 having a fluid reservoir 42 that may be fabricated of a collapsible material. In such a case, external pressure may be applied thereto so as to force the fluid medication contained therein into the second housing structure 18.

Figure 3:
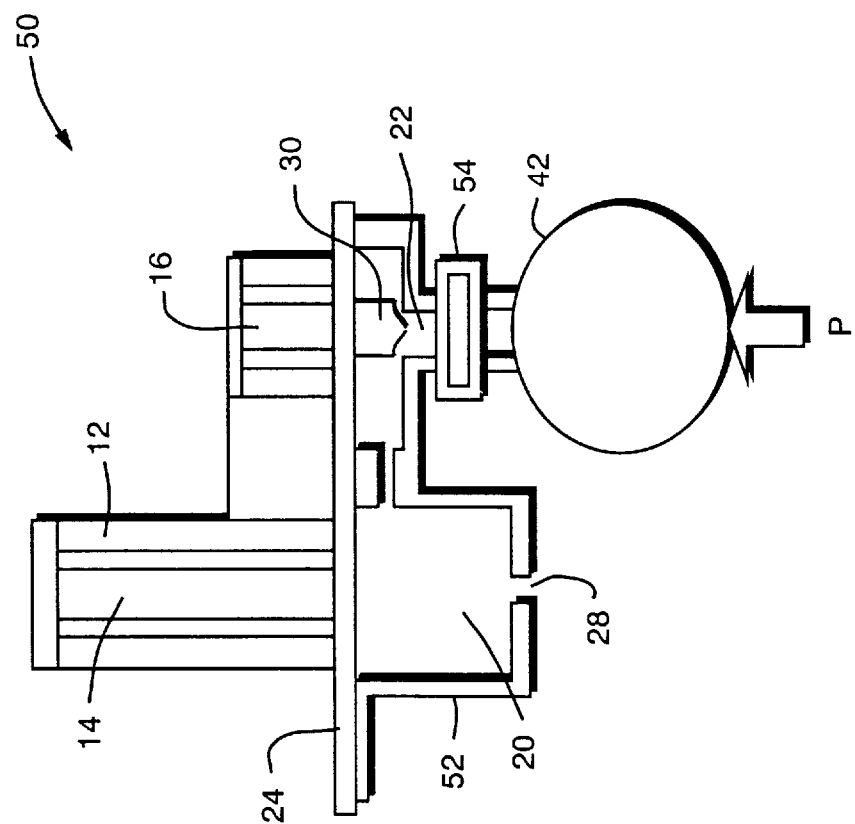
FIG. 3 is a functional block diagram of the delivery system shown in FIG. 2 with an alternate second housing structure.

The second housing structure 18 may also take many different forms. For instance, referring to FIG. 3, there is shown a third embodiment of a solid state needleless injection system 50 having a first housing structure 52 that has a luer-lock interface 54 formed therein for connection with the fluid reservoir 42. Such an interface 54 allows for quick and easy attachment and removal of the fluid reservoir 42 from the first housing structure 52.

Throughout all of the above-described embodiments, an external electrical excitation (not shown) is required for the first piezoelectric element 14, the second piezoelectric element 16, and the electromechanical actuator (not shown). Such external electrical excitation typically comprises a DC voltage source having electrodes which are attached to the piezoelectric materials and to the coil, respectively.

With the present invention method now fully described, it can thus be seen that the primary objective set forth above is efficiently attained and, since certain changes may be made in the above-described embodiments without departing from the scope of the invention, it is intended that all matter contained in the above description or shown in the accompanying drawings shall be interpreted as illustrative and not restrictive, the scope of the invention being defined in the appended claims.

What is claimed is:

1. An apparatus for the rapid and repeatable delivery of small quantities of a fluid to an intended target, comprising:
    at least one first housing having walls defining a dispensing chamber for said fluid, and at least one nozzle element defined in one of said walls for the discharge of said fluid; and
    at least one second housing communicating with said first housing, said second housing comprising pump means comprising at least one piezoelectric element in fluid communication with said first housing for forcing a predetermined quantity of said fluid out of said dispensing chamber and through said at least one nozzle element, said second housing being detachable from said first housing, and actuation means for exciting said pump means to force said fluid out of said dispensing chamber.

2. The apparatus according to claim 1, wherein said first housing includes a fluid reservoir for holding the quantity of fluid to be dispensed, said fluid reservoir in fluid communication with said dispensing chamber, and a valve assembly for controlling the quantity and rate of transfer of fluid from said fluid reservoir to said dispensing chamber.

3. The apparatus according to claim 1, wherein said at least one of said walls is deformable and adapted to deflect and to modulate the size of said dispensing chamber.

4. The apparatus according to claim 3, wherein said deformable wall comprises a flexible membrane positioned for communication with said pump means.

5. The apparatus according to claim 2, wherein said second housing is adapted for detachable association with said first housing.

6. The apparatus according to claim 1, wherein said first housing is disposable.

7. The apparatus according to claim 1 wherein said apparatus is portable and said actuation means comprises a battery.

8. The apparatus according to claim 1, wherein plural nozzle elements are defined.

9. The apparatus according to claim 1, wherein plural piezoelectric elements are present, and a first piezoelectric element is associated with said dispensing chamber, and a second piezoelectric element is associated with said valve assembly.

10. The apparatus according to claim 1, further including secondary pump means associated with said fluid reservoir to place pressure on said reservoir to expel fluid contained therein.

11. The apparatus according to claim 10, wherein said secondary pump means comprises a spring-biased plunger disposed within said reservoir.

12. A solid state needleless injection system that utilizes piezoelectric materials to forcibly introduce fluid medication through the skin of a patient, said system comprising:
    a first housing having at least one wall and defining a dispensing chamber of variable volume formed therein, said dispensing chamber having an output port and an opening formed therein; and
    a second housing located in communication with said first housing, said second housing having at least one wall and defining a first piezoelectric actuator, said first piezoelectric actuator being disposed in fluid communication with a wall of said first housing proximate said dispensing chamber, and being excitable so as to provide a driving force against said wall to thereby force fluid from within said dispensing chamber through said output port.

13. The system according to claim 12, wherein said dispensing chamber also has an input port formed therein, wherein said input port allows fluid to enter into said dispensing chamber.

14. The system according to claim 13, further comprising a fluid reservoir, said fluid reservoir having an output port formed therein, said output port of said fluid reservoir being operatively connected to said input port of said dispensing chamber so as to allow said fluid to flow from said fluid reservoir to said dispensing chamber.

15. The system according to claim 14, further comprising a valve assembly operatively connected between said output port of said fluid reservoir and said input port of said dispensing chamber so as to control the flow of fluid between said fluid reservoir to said dispensing chamber.

16. The system according to claim 15, wherein said valve assembly comprises:
    a valve seat formed in said first housing;
    a valve stop formed in said first housing and positioned to cooperate with said valve seat to alternately permit and prevent the flow of fluid from said fluid reservoir to said dispensing chamber; and
    an actuation means for controlling the position of said valve stop with respect to said valve seat.

17. The system according to claim 16, wherein said actuation means comprises a second piezoelectric element, said second piezoelectric element being disposed proximate the wall adjacent said valve stop, and being excitable so as to provide a driving force against said wall and thereby force said valve stop against said valve seat.

18. The system according to claim 17, wherein said second rigid housing having a means for disposing said first piezoelectric actuator proximate said wall and said dispensing chamber and disposing said second piezoelectric actuator proximate said valve stop.

19. The system according to claim 16, wherein said actuation means comprises an electromechanical actuator, said electromechanical actuator being disposed proximate said wall and said dispensing chamber, and being excitable so as to provide a driving force against said wall and thereby force said valve stop against said valve seat.

20. A solid state needleless injection method that utilizes piezoelectric materials to forcibly introduce fluid medication into the skin of a patient, said method comprising the steps of:
    providing a first housing, said having a dispensing chamber formed therein, said dispensing chamber having an output port and an opening formed therein;
    positioning a first piezoelectric actuator in fluid communication with said first housing and proximate a wall of said first housing; and exciting said first piezoelectric actuator so as to provide a driving force against said wall and thereby force fluid medication from within said dispensing chamber through said output port.

21. The method according to claim 20, further comprising the steps of:

providing an input port in said dispensing chamber;

connecting a fluid reservoir containing fluid medication to said input port; and replenishing said dispensing chamber with fluid medication from said fluid reservoir by allowing fluid medication to flow from said fluid reservoir to said dispensing chamber through said input port.

22. The method according to claim 21, further comprising the step of controlling the flow of fluid medication from said fluid reservoir to said dispensing chamber.

* * * * *

UNITED STATES PATENT AND TRADEMARK OFFICE
CERTIFICATE OF CORRECTION

PATENT NO. : 5,840,062
DATED : November 24, 1998
INVENTOR(S) : Gumaste et al

It is certified that error appears in the above-identified patent and that said Letters Patent is hereby corrected as shown below:

Claim 20, Col. 8, line 62, insert - -first housing- - after "said".

Signed and Sealed this

Seventh Day of December, 1999

Attest:

Q. TODD DICKINSON

*Attesting Officer*  *Acting Commissioner of Patents and Trademarks*